United States Patent
Nakazawa et al.

(10) Patent No.: US 10,420,736 B2
(45) Date of Patent: Sep. 24, 2019

(54) ANTIOXIDIZING INTRAOCULAR PERFUSION SOLUTION

(71) Applicant: TOHOKU UNIVERSITY, Miyagi (JP)

(72) Inventors: Toru Nakazawa, Miyagi (JP); Takaaki Akaike, Miyagi (JP); Hiroshi Kunikata, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 15/762,726

(22) PCT Filed: Sep. 30, 2016

(86) PCT No.: PCT/JP2016/079191
§ 371 (c)(1),
(2) Date: Jun. 4, 2018

(87) PCT Pub. No.: WO2017/057768
PCT Pub. Date: Apr. 6, 2017

(65) Prior Publication Data
US 2018/0296504 A1    Oct. 18, 2018

(30) Foreign Application Priority Data

Sep. 30, 2015 (JP) .................... 2015-194716

(51) Int. Cl.
| | | |
|---|---|---|
| *A61K 31/16* | (2006.01) |
| *A61K 38/00* | (2006.01) |
| *A61K 31/198* | (2006.01) |
| *A61P 27/02* | (2006.01) |
| *A61K 31/4162* | (2006.01) |
| *A61K 45/06* | (2006.01) |
| *A61P 41/00* | (2006.01) |
| *A61P 43/00* | (2006.01) |
| *A61K 9/00* | (2006.01) |
| *A61K 9/08* | (2006.01) |

(52) U.S. Cl.
CPC ............ *A61K 31/16* (2013.01); *A61K 9/0048* (2013.01); *A61K 9/08* (2013.01); *A61K 31/198* (2013.01); *A61K 31/4162* (2013.01); *A61K 38/00* (2013.01); *A61K 45/06* (2013.01); *A61P 27/02* (2018.01); *A61P 41/00* (2018.01); *A61P 43/00* (2018.01)

(58) Field of Classification Search
CPC ...... A61K 31/16; A61K 31/4162; A61P 27/02
See application file for complete search history.

(56) References Cited

U.S. PATENT DOCUMENTS

| | | | |
|---|---|---|---|
| 5,221,537 A | 6/1993 | Hecht et al. | |
| 5,466,673 A * | 11/1995 | Ohmori ............... | A61K 9/0048 514/20.8 |
| 5,500,445 A | 3/1996 | Matsumoto et al. | |
| 2009/0264375 A1 * | 10/2009 | Shah .................... | A61K 9/0048 514/23 |
| 2011/0251137 A1 | 10/2011 | Chen et al. | |

FOREIGN PATENT DOCUMENTS

| | | |
|---|---|---|
| JP | 7-010701 | 1/1995 |
| JP | 7-97331 | 4/1995 |
| JP | 2013-523831 | 6/2013 |
| WO | WO-96/00055 A1 | 1/1996 |
| WO | WO-2009/086073 A1 | 7/2009 |

OTHER PUBLICATIONS

Sawa et al., "Takusan Tsunagaru S-polysulfur-ka Cysteine no Seisei Kiko to Kino", Experimental Medicine, vol. 32, No. 15, special extra issue, 2014, pp. 46-50 with partial English translation.
Ida et al., "Reactive Cysteine Persulfides and S-polythiolation Regulate Oxidative Stress and Redox Signaling", PNAS, vol. 111, No. 21, 2014, pp. 7606-7611.
Search Report in International Application No. PCT/JP2016/079191 dated Oct. 25, 2016, 2 pages.
International Preliminary Report on Patentability in International Application No. PCT/JP2016/079191 dated Apr. 12, 2018, 6 pages.
Kunikata et al., "Metabolomic Profiling of Reactive Persulfides and Polysulfides in the Aqueous and Vitreous Humors", Scientific Reports, vol. 7, No. 1, 2017, 10 pages.
Search Report in EP Application No. 16851937.9 dated May 17, 2019, 9 pages.

* cited by examiner

*Primary Examiner* — Sudhakar Katakam
(74) *Attorney, Agent, or Firm* — Marshall, Gerstein & Borun LLP (57) ABSTRACT

The present invention addresses the problem of providing an intraocular irrigating solution that allows the intraocular tissue to be sufficiently protected during ophthalmic surgery and further has high safety. The problem is solved by an intraocular irrigating solution containing at least one of active sulfur molecules of which examples include cysteine persulfide and glutathione persulfide.

5 Claims, 14 Drawing Sheets

ANTIOXIDIZING INTRAOCULAR PERFUSION SOLUTION

TECHNICAL FIELD

The present invention relates to intraocular irrigating solutions. More specifically, the present invention relates to a novel intraocular irrigating solution containing an active sulfur molecule.

BACKGROUND ART

In ophthalmic surgery such as treatment of cataract, corneal transplantation, or vitreous surgery, an intraocular irrigating solution is used to protect the intraocular tissue during the surgery.

An intraocular irrigating solution containing a glutathione derivative has been developed as such an intraocular irrigating solution and has been considered to be a very stable intraocular irrigating solution that effectively suppresses precipitation of calcium (see Patent Literature 1).

Moreover, an intraocular irrigating solution containing a phosphoric diester of ascorbic acid and the tocopherol has also been developed and considered to be excellent in protection of corneal cells and to enable ophthalmic surgery to be safely performed (see Patent Literature 2).

However, cysteine persulfide (CysSSH) as an active sulfur molecule has been reported to be produced in vivo. For example, pyridoxal phosphate (PLP) well known as a coenzyme such as a deaminase has been reported to directly react with cystine to produce CysSSH. Moreover, a cysteine residue in the active center of a certain enzyme, particularly rhodanese known as an enzyme for detoxifying cyan ($CN^-$), has been known to receive a sulfur molecule supplied from a thiosulfate ion to form a persulfide, which reacts with a cyanide ion and subjected to metabolic detoxification into a thiocyanate ion ($SCN^-$).

Commonly, CysSSH had been recognized as an unstable metabolic intermediate responsible for the catalytic activity of such a special enzyme. However, the present inventor found that an active sulfur molecule such as CysSSH in vivo exhibits high antioxidant activity and the function of controlling a redox signal (see Non Patent Literature 1).

PRIOR ART

Patent Literature

Patent Literature 1: Japanese Patent Laid-Open No. 7-97331
Patent Literature 2: Japanese Patent Laid-Open No. 7-10701

Non Patent Literature

Non Patent Literature 1: Ida, T. et al. Reactive cysteine persulfides and S-polythiolation regulate oxidative stress and redox signaling. Proc. Natl. Acad. Sci. USA, 2014, doi: 10.1073/pnas. 1321232111

SUMMARY OF THE INVENTION

Technical Problem to be Solved

A case in which an intraocular irrigating solution results in decreased vision after ophthalmic surgery while protecting the intraocular tissue sporadically occurs in ophthalmic surgery. The present inventors consider that examples of the cause of the case include corneal opacity, lens opacity, and retinal cell death due to oxidative stress caused by operation invasion. In other words, the present inventors consider that in ophthalmic surgery, an abundance of an intraocular irrigating solution for surgery is always circulated during the surgery because of to the nature of the ophthalmic surgery, and the intraocular irrigating solution causes operation invasion because of continuing to directly contact with each intraocular tissue.

The present invention solves such problems. An object of the present invention is to provide an intraocular irrigating solution that allows the intraocular tissue to be sufficiently protected during ophthalmic surgery and further has high safety.

Means to Solve the Technical Problem

As a result of repeating diligent study in order to solve the above-described problems, the present inventors found that the intraocular tissue of a patient having a disease requiring ophthalmic surgery is in the state of having the higher concentration of active sulfur molecules than that in the intraocular tissue of a healthy subject. In addition, it was found, on the basis of an estimation that poor prognosis after ophthalmic surgery is caused by oxidative stress caused by operation invasion, that an intraocular irrigating solution that allows the intraocular tissue to be sufficiently protected during ophthalmic surgery and further has high safety can be provided by using an active sulfur molecule with antioxidant activity found by the present inventors as a component of the intraocular irrigating solution. The present invention was thus accomplished.

In other words, the present invention is to provide an intraocular irrigating solution comprising one or more selected from the group consisting of active sulfur molecules represented by Formula (1) and Formula (2), and derivatives of the active sulfur molecules:

(in the above Formula (1), $R^1$ is selected from amino acids and polypeptides having a thiol group and represents a moiety other than the thiol group, and n is an integer 1 or more); and (in the above Formula (2), $R^2$ and $R^3$ are independently selected from amino acids and polypeptides having a thiol group and each represent a moiety other than the thiol group, and n is an integer 2 or more).

Moreover, a preferred embodiment of the present invention is an embodiment in which the $R^1$, $R^2$, and $R^3$ are L-cysteine (Cys), homocysteine (Hcys), or glutathione (GSH) and each represent a moiety other than a thiol group.

Moreover, a preferred embodiment of the present invention is an embodiment in which the active sulfur molecules comprise one or more selected from cysteine persulfide and glutathione persulfide.

Advantageous Effects of Invention

According to the present invention, an intraocular irrigating solution that allows the intraocular tissue to be sufficiently protected during ophthalmic surgery and further has high safety can be provided. In other words, as found by the present inventor as described above, an active sulfur molecule has a high antioxidant action, and therefore, use of the active sulfur molecule in an intraocular irrigating solution enables oxidative stress caused by operation invasion to be sufficiently suppressed. Moreover, the intraocular tissue of a patient having a disease requiring ophthalmic surgery is in the state of having the higher concentration of active sulfur molecules than that in the intraocular tissue of a healthy subject, and the intraocular irrigating solution of the present invention contains active sulfur molecules existing in an eye of the patient. Therefore, the intraocular irrigating solution is an intraocular irrigating solution having a very high affinity in the eye and having high safety.

BRIEF DESCRIPTION OF DRAWINGS

FIG. 7A-1 is a graph indicating the standard peaks of various active sulfur molecules (GSSG, GSSSG, GSSSSG, and GSSSSSG).

FIG. 7A-2 is a graph indicating standard curves at three points using GSSG having known concentrations (1 μM, 10 μM and 50 μM).

DESCRIPTION OF EMBODIMENTS

Embodiments of the present invention will be described in detail below. However, the present invention is not limited to the following embodiments but may be variously modified within the scope of the gist of the present invention.

An intraocular irrigating solution which is an embodiment of the present invention comprises an active sulfur molecule or an active sulfur molecule derivative.

Such active sulfur molecules are represented by the following Formulae (1) and (2):

It is preferable that in the above Formula (1), $R^1$ is selected from amino acids and polypeptides having a thiol group and is L-cysteine (Cys), homocysteine (Hcys), or glutathione (GSH). $R^1$ is an amino acid or a polypeptide having a thiol group and represents a moiety other than a thiol group. Moreover, n is an integer 1 or more, which may be 2 or more and of which the upper limit is not particularly set but is, for example, 10 or less, may be 8 or less, and may be 5 or less.

In other words, if L-cysteine is taken as an example of a compound represented by Formula (1), the compound is a compound having a structure in which surplus sulfur is further bound to the thiol group of L-cysteine, as described below.

[Chem 1]

Structures (L-Shaped Structures) of Cysteine and Cysteine Persulfide

It is preferable that in the above Formula (2), $R^2$ and $R^3$ are independently selected from amino acids and polypeptides having a thiol group and are L-cysteine, homocysteine, or glutathione. $R^2$ and $R^3$ are an amino acid or a polypeptide having a thiol group and each represent a moiety other than the thiol group. Moreover, n is an integer 2 or more, which may be 3 or more and of which the upper limit is not particularly set but is, for example, 10 or less, may be 8 or less, and may be 5 or less.

Examples of the molecule represented by the above Formula (1) include cysteine persulfide (CysSSH), glutathione persulfide (GSSH), homocysteine persulfide (HcysSSH), and molecules in which sulfur is further bound thereto. Furthermore, examples of the molecules in which sulfur is bound include, but are not limited to, CysSSSH, CysSSSSH, GSSSH, and GSSSSH.

In the present specification, GSH is represented as the trivial name of glutathione, GSSH represents a compound having a structure in which one sulfur molecule is bound to the thiol group of glutathione, and CysSSH represents cysteine persulfide which is a compound having a structure in which one sulfur molecule is bound to the thiol group of L-cysteine.

Moreover, examples of a derivative of the molecule represented by the above Formula (1) include derivatives in which an amino group, a carboxyl group, or the like is substituted by an optional substituent in an amino acid and a polypeptide chain included in $R^1$. Examples of such derivatives include silylated bodies, esterified bodies, acylated bodies, and acetylated bodies.

Examples of the molecule represented by the above Formula (2) include a molecule (CysSSSCys) in which sulfur is bound to cystine, a molecule (HcysSSSHcys) in which sulfur is bound to homocystine, a molecule (GSSSG) in which sulfur is bound to oxiglutatione, and molecules in which sulfur is further bound thereto. Examples of the molecules in which sulfur is further bound include, but are not limited to, CysSSSSCys and GSSSSG.

Examples of a derivative of the molecule represented by the above Formula (2) include derivatives similar to the derivatives in the above Formula (1).

Figure 1:
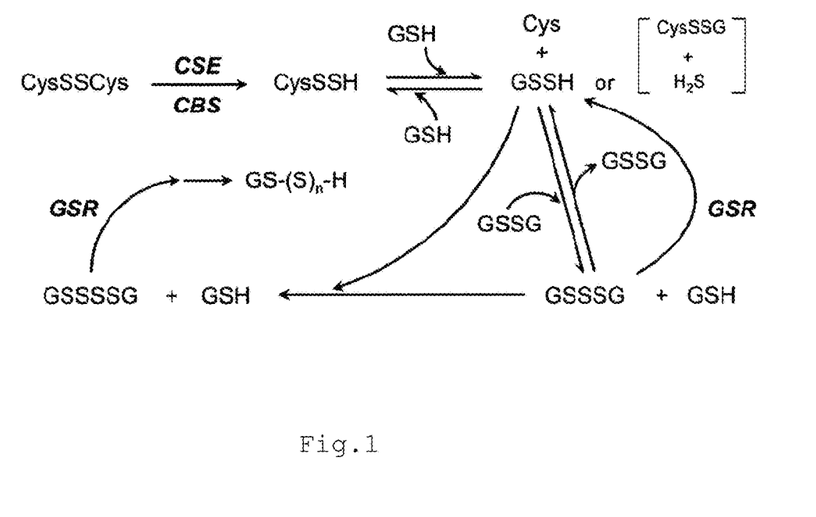
FIG. 1 is a view illustrating a mechanism of production of in vivo active persulfide.

As described above, such active sulfur molecules are known to be produced in vivo. Moreover, the present inventors reveal the mechanism of production of in vivo active persulfide, illustrated in FIG. 1. Those skilled in the art can obtain active sulfur molecules by using the in vivo mechanism to produce active sulfur molecules and extracting and producing the active sulfur molecules.

The concentration of active sulfur molecules contained in the intraocular irrigating solution varies according to a symptom in a patient intended to use the intraocular irrigating solution or the kind of the active sulfur molecules, but is typically 0.0003 µg/mL or more, may be 0.003 µg/mL or more, may be 0.01 µg/mL or more, may be 0.03 µg/mL or more, may be 0.1 µg/mL or more, may be 0.3 µg/mL or more, may be 1 µg/mL or more, may be 3 µg/mL or more, may be 10 µg/mL or more, and may be 30 µg/mL or more, in terms of final concentration. In contrast, the upper limit thereof is typically 1,000 µg/mL or less, may be 300 µg/mL or less, may be 100 µg/mL or less, and may be 30 µg/mL or less.

A component typically blended into an intraocular irrigating solution may be blended into the intraocular irrigating solution according to the embodiment of the present invention. Examples of such components include: various electrolytes such as calcium chloride, magnesium chloride, magnesium sulfate, sodium acetate, sodium phosphate, potassium phosphate, sodium citrate, and sodium hydrogen carbonate; monosaccharides such as glucose; peptides such as glutathione; and antibiotics such as penicillin. These components in normal amounts can be blended.

A method for producing the intraocular irrigating solution according to the embodiment of the present invention is not particularly limited. The intraocular irrigating solution is prepared according to a known method. For example, a blending component containing active ion molecules is dissolved in sterilized pure water, and the resulting solution is then adjusted to desired pH with a pH adjuster such as hydrochloric acid or sodium hydroxide. The solution adjusted to the desired pH is filtrated and then subjected to heat sterilization treatment. The intraocular irrigating solution can be produced by air-cooling the solution subjected to the sterilization treatment.

The intraocular irrigating solution according to the embodiment of the present invention contains active ion molecules with high antioxidant activity and therefore enables high oxidative stress in ophthalmic surgery to be canceled. Therefore, the intraocular irrigating solution enables less invasion in ophthalmic surgery to be achieved and enables the intraoperative and postoperative destruction of the intraocular tissue to be minimized.

EXAMPLES

The present invention will be described in more detail below with reference to Examples.

<Analysis of Intraocular Environment of Patient with Diabetic Retinopathy>

Eighteen patients (having an average age of 57.7±16.1 and consisting of 9 males and 9 females) with diabetic retinopathy who were hospitalized and underwent surgery under medical treatment in the Department of Ophthalmology at the Tohoku University Hospital were enrolled in a diabetic retinopathy disease group. Moreover, 22 patients (having an average age of 71.0±13.4 and consisting of 9 males and 13 females) with cataract or noninflammatory macular disease (epiretinal membrane or macular hole) were enrolled in a control group. Each patient was treated with broad-spectrum ophthalmic solution for preoperative sterilization therapy four times a day for three consecutive days before the surgery. Samples of blood, aqueous humor, and the vitreous body were collected on the surgery day. About 1 mL of the blood sample was collected in vein root access before the surgery and was centrifugalized, followed by cryopreserving plasma. In the cataract surgery, anterior chamber paracentesis was performed to collect about 100 pL of the aqueous humor sample, which was cryopreserved. In the vitreous surgery, vitrectomy (combination of posterior vitrectomy and removal of epiretinal membrane, proliferative membrane, or internal limiting membrane depending on pathology) was performed, and about 100 pL of the removed vitreous body sample was cryopreserved. For postoperative anti-inflammatory effect, each patient continued to be treated with steroidal anti-inflammatory ophthalmic solution four times a day and further with non-steroidal anti-inflammatory ophthalmic solution twice a day for one or more months from the day after the surgery. Moreover, for prevention of postoperative infections, each patient continued to be treated with broad-spectrum ophthalmic solution four times a day for one or more months from the day after the surgery.

The features of the patients with diabetic retinopathy are set forth in Table 1.

TABLE 1

Features of Patients with Diabetic Retinopathy

|  | Patients with diabetic retinopathy | Control | P value |
|---|---|---|---|
| Number | 18 | 22 |  |
| Age (years old) | 57.7 ± 16.1 | 71.0 ± 13.4 | 0.007 |
| Sex (male:female) | 9:9 | 9:13 | 0.565[a] |
| Body weight (kg) | 58.6 ± 13.6 | 60.3 ± 9.9 | 0.652 |
| Hemoglobin concentration (%) | 7.5 ± 2.0 | 5.9 ± 0.8 | 0.004 |
| Glucose concentration (mg/dL) | 175.4 ± 74.8 | 101.0 ± 14.9 | <0.001 |
| Total cholesterol concentration (mg/dL) | 182.1 ± 45.1 | 187.3 ± 39.4 | 0.701 |
| Urea nitrogen concentration (mg/dL) | 19.5 ± 7.1 | 14.9 ± 2.9 | 0.009 |
| Creatinine concentration (mg/dL) | 1.1 ± 0.6 | 0.8 ± 0.2 | 0.04 |

*P value: two-sample t-test (a: chi-square test)

The concentrations of active sulfur molecules in the plasma, aqueous humor, and vitreous bodies from the patients in the diabetic retinopathy disease group and the control group were measured by metabolome analysis.

Figure 2:
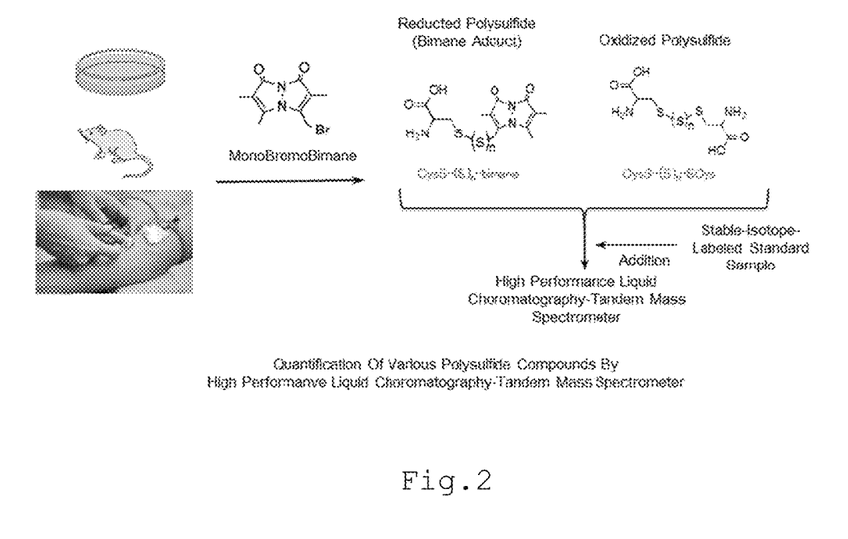
FIG. 2 is a view illustrating the principle of metabolome analysis.

An active ion molecule which is a reduced polysulfide has high chemical reactivity and is unstable, and it is difficult to directly identify and quantify the active ion molecule. Therefore, the sample was allowed to react with monobromobimane as an alkylating reagent for a thiol group to convert a reduced polysulfide in the sample into a stable polysulfide-bimane adduct. Standard samples of various stable-isotope-labeled polysulfide-bimane adducts and oxidized polysulfides in known amounts were added to the sample, and various unlabeled and stable-isotope-labeled polysulfide-bimane adducts and oxidized polysulfides were measured using LC-MS/MS (Agilent Technologies International Japan, Ltd., 6430). A method for synthesizing the stableisotope-labeled standard sample and the conditions of the measurement of the various polysulfide-bimane adducts and oxidized polysulfides in LC-MS/MS conformed to a method disclosed in Non Patent Literature 1. The concentrations of the various polysulfides in the sample were calculated based on signal intensity in LC-MS/MS chromatogram of the added stable-isotope-labeled standard sample in a known amount. The principle of the measurement is illustrated in FIG. 2.

Moreover, the various polysulfide-related standard samples were prepared according to a method disclosed in Non Patent Literature 1. Specifically, P-NONOate (0.5 mM) was added to 0.5 mM cysteine, glutathione, or homocysteine dissolved in a 10 mM Tris-HCl buffer solution (pH 7.4), the resultant was left to stand for 15 minutes at room temperature, and NaHS (0.5 mM) was then added to be allowed to react for 15 minutes at room temperature to produce a reduced polysulfide. Since the reduced polysulfide was unstable, the reduced polysulfide converted into a stable polysulfide-bimane adduct by allowing the reduced polysulfide to react with monobromobimane (5 mM) as an alkylating reagent for a thiol group. Each polysulfide-bimane adduct in the reaction liquid and the oxidized polysulfides produced by autoxidation were separated and purified by high performance liquid chromatography to form standard samples.

Figure 3:
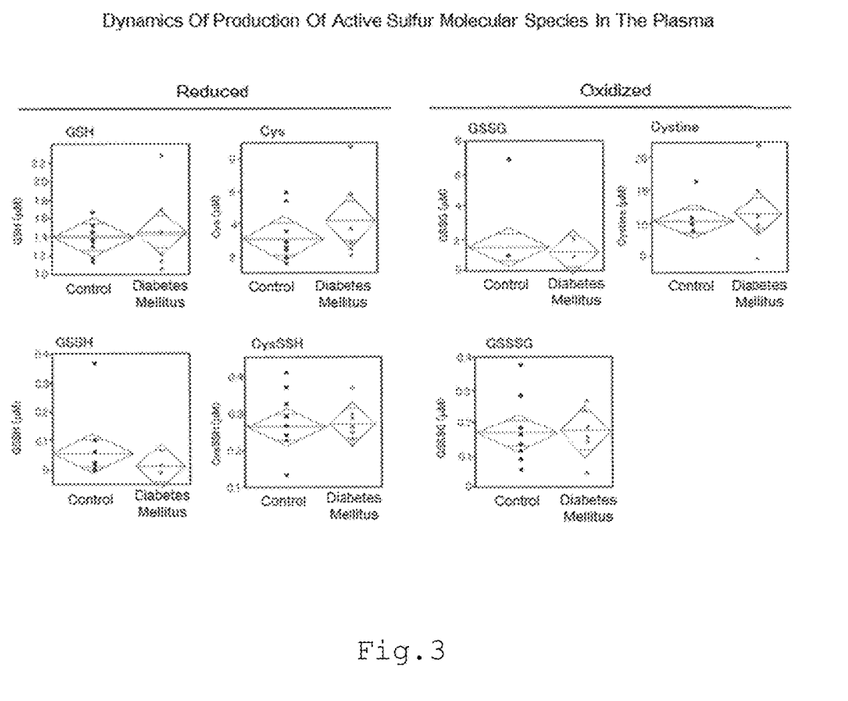
FIG. 3 is a graph indicating comparison of the concentrations of sulfur-related substances in the plasma of patients with diabetic retinopathy and controls.
Figure 4:
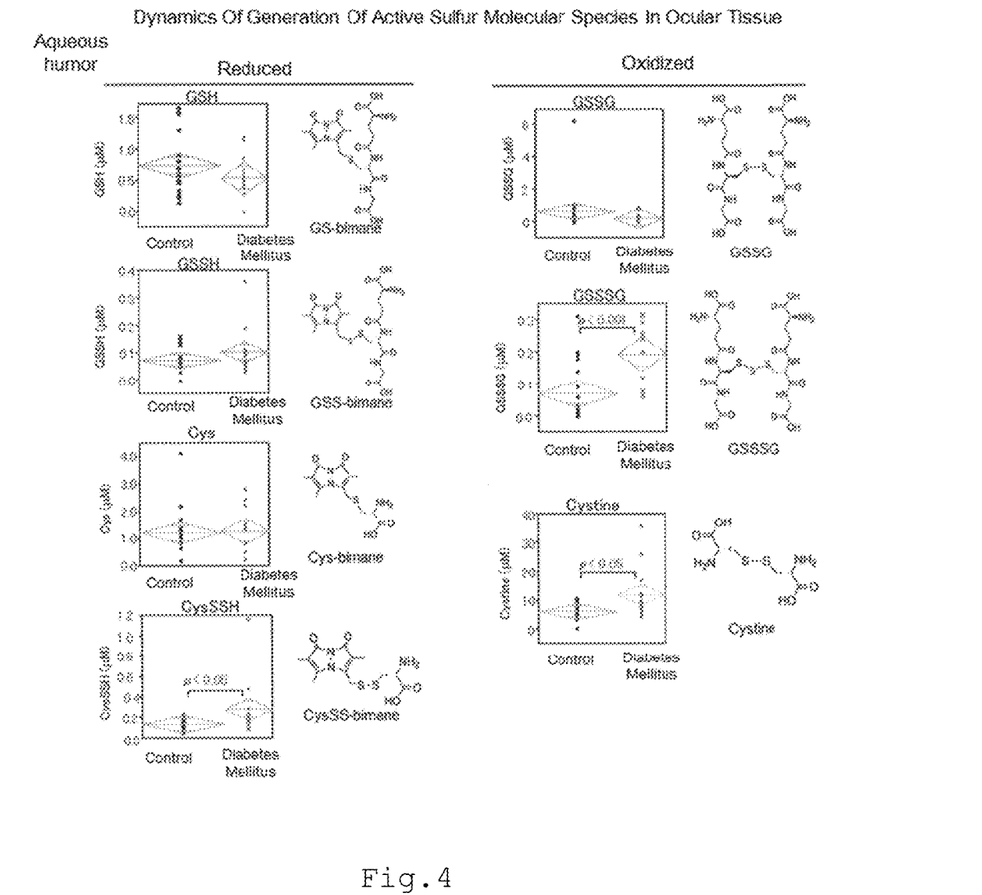
FIG. 4 is a graph indicating comparison of the concentrations of sulfur-related substances in the aqueous humor of patients with diabetic retinopathy and controls.
Figure 5:
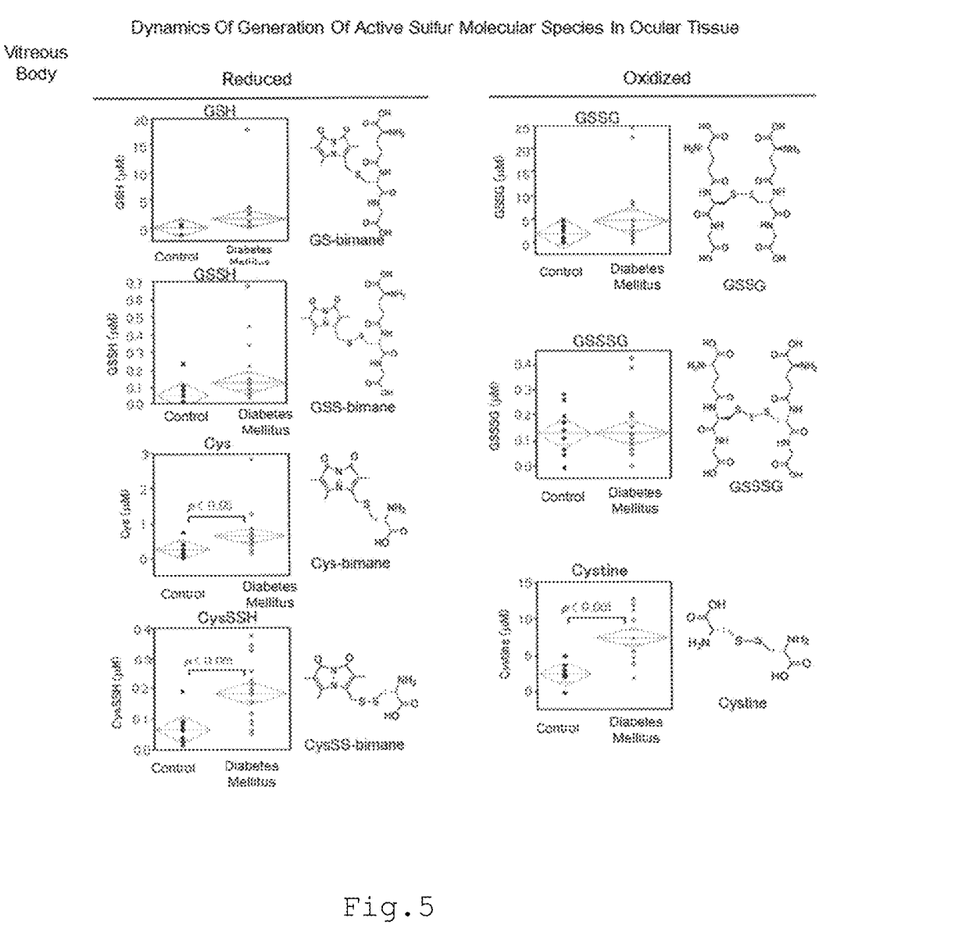
FIG. 5 is a graph indicating comparison of the concentrations of sulfur-related substances in the vitreous bodies of patients with diabetic retinopathy and controls.

The results are illustrated in FIG. 3 to FIG. 5.

FIG. 3 shows results that there is no difference in the concentration of active sulfur molecules in plasma in comparison between the diabetic retinopathy disease group and the control group.

FIG. 4 shows results that the concentrations of active sulfur molecules in aqueous humor are higher in the diabetic retinopathy disease group in comparison between the diabetic retinopathy disease group and the control group.

FIG. 5 shows results that the concentrations of active sulfur molecules in the vitreous body are higher in the diabetic retinopathy disease group in comparison between the diabetic retinopathy disease group and the control group.

As is clear from the results of FIG. 3 to FIG. 5, there was no tendency that the concentrations of active sulfur molecules such as cysteine persulfide and glutathione persulfide in plasma were increased in the diabetic retinopathy disease group. In contrast, there was a tendency that the concentrations of active sulfur molecules such as cysteine persulfide and glutathione persulfide in aqueous humor and vitreous body, i.e., in the intraocular tissue were increased in the diabetic retinopathy disease group.

The reason why the concentrations of active sulfur molecules were increased in the diabetic retinopathy disease group is unclear. However, the accumulation of oxidative stress is known to be involved in the pathology of diabetic retinopathy, and it is presumed that the defense mechanism of the living body functions to produce an antioxidant in an eye.

The active sulfur molecules are highly safe substances that have very high antioxidant activity in comparison with glutathione included in a conventional intraocular irrigating solution and that can be confirmed to exist in the eyes not only in the intraocular disease patient but also in the control group.

The oxidative stress due to ophthalmic surgery is considered to affect the cornea, the lens, and the retina, and the intraocular irrigating solution according to the embodiment of the present invention has high antioxidant activity and therefore enables the intraocular exposure of oxidative stress to be prevented. Therefore, cases in which after ophthalmic surgery, corneal endothelium exhaustion proceeds, resulting in bullous keratopathy, cases in which after lens-sparing vitreous surgery, crystalline lens nucleus sclerosis proceeds, resulting in cataract, and cases in which in vitreous surgery, retinal cell death proceeds, resulting in poor postoperative visual function can be reduced.

In other words, the intraocular irrigating solution according to the embodiment of the present invention contains high-concentration active sulfur molecules existing in the intraocular environment of a patient with an intraocular disease and can be therefore considered to be an intraocular irrigating solution that has a high affinity and is very safe in an eye. In addition, the intraocular irrigating solution has high antioxidant activity and therefore enables the destruction of the intraocular tissue after ophthalmic surgery to be suppressed and poor prognosis to be greatly improved.

The effect of protecting cells by active sulfur molecules such as cysteine persulfide and glutathione persulfide will now be investigated.

An example of preparation of $GS(S)_nG$ will be described below. Such active sulfur molecules may be prepared by a method different from this method.

<Reagent>
Reduced glutathione (GSH): SIGMA-ALDRICH, G4251-5G (M. W=307.2)

Sodium disulfide ($Na_2S_2$): DOJINDO LABORATORIES, SB02

0.1% Formic acid (300 mL of MilliQ water+300 μL of formic acid)

0.1% Formic acid/60% methanol (80 mL of 0.1% formic acid+120 mL of methanol)

Figure 6:
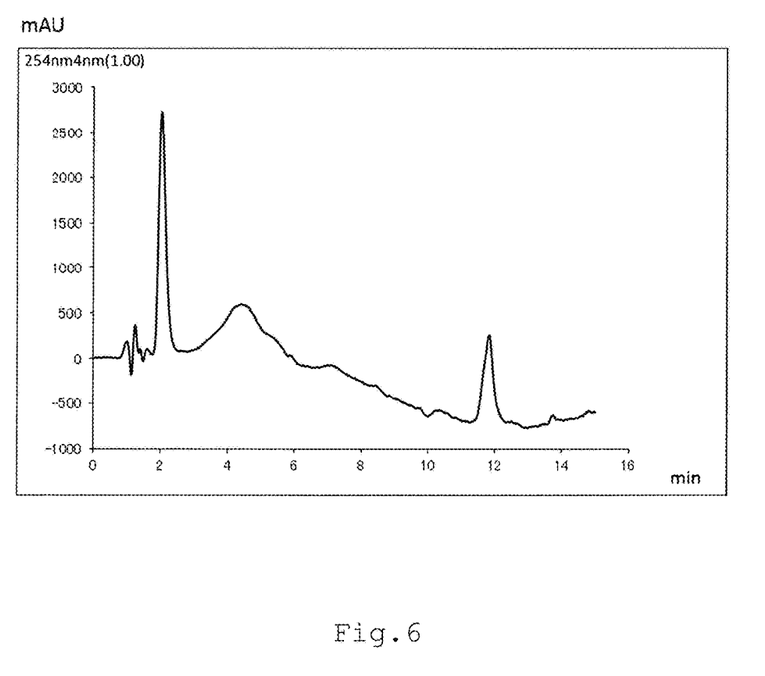
FIG. 6 is a graph indicating the results of HPLC analysis of a washed sample.
Figure 7A:
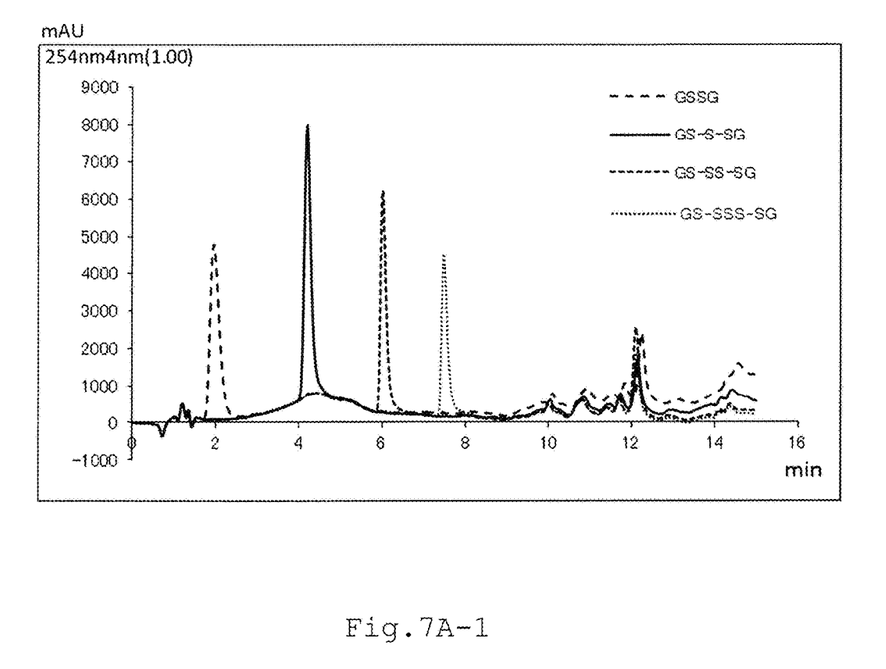
Figure 7A:
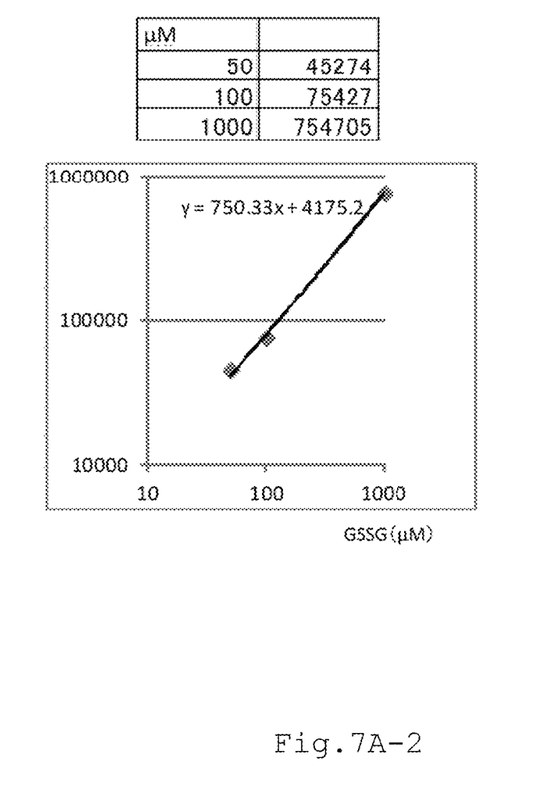
Figure 7B:
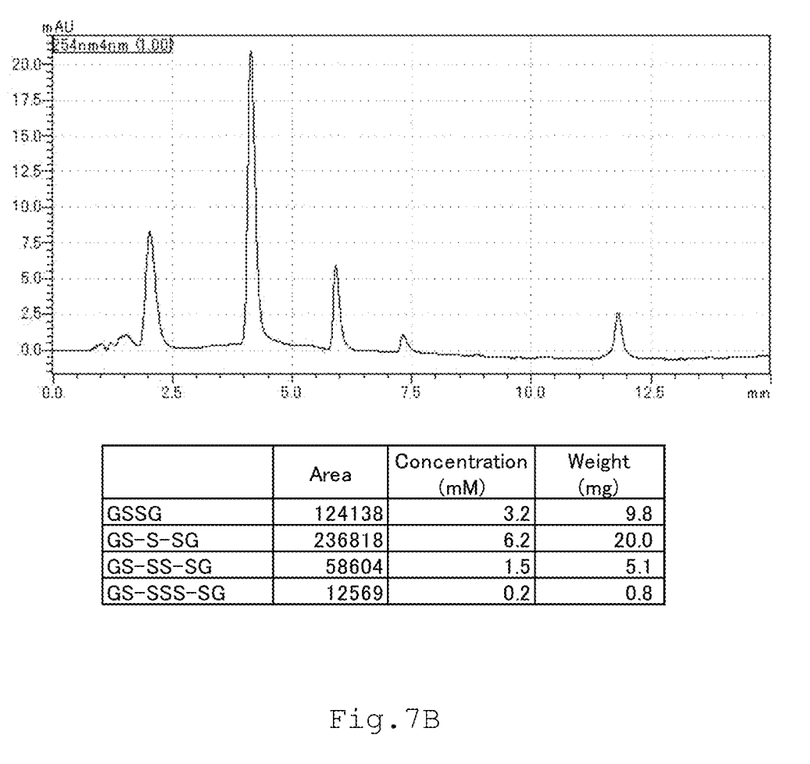
FIG. 7B illustrates a graph (upper) indicating the results of HPLC measurement of a sample (before being washed) just after being synthesized and a table (lower) indicating the results of quantification of various active sulfur molecules.

<Method>
1. A Sep-pak column was equilibrated with 0.1% formic acid (100 mL).
2. Ultrapure water in which GSH and $Na_2S_2$ were dissolved was degassed and subjected to argon substitution.
3. GSH and $Na_2S_2$ were weighed to prepare 200 mM GSH and 200 mM $Na_2S_2$ (31.4 mg of GSH+511 μL of MilliQ water) (11.1 mg of $Na_2S_2$+505 μL of MilliQ water).
4. In an Eppendorf tube, 0.5 mL of 200 mM GSH and 0.5 mL of 200 mM $Na_2S_2$ were mixed and allowed to react with each other for 15 minutes at room temperature.
5. To a tube, 15 mL of the resultant in the above "4" was transferred, and 4 mL of 0.1% formic acid was added to stop the reaction.
6. The tube in the above "5" was centrifugalized (9,000 rpm, 10 min), and 10 μL of a supernatant (sample just after synthesis) was collected for HPLC confirmation.
7. All of the supernatant in "6" was loaded into the equilibrated Sep-pak column.
8. Washing: Washed samples were obtained by allowing 200 mL of 0.1% formic acid to flow (allowing 85 mL to flow, followed by collecting 12 samples of which each was 10 mL).
9. Elution: Elution samples were obtained by collecting 0.1% formic acid/60% methanol at 10 mL×6 samples.
10. The obtained washed samples and the sample just after the synthesis were confirmed by HPLC (90 μL of 0.1% formic acid+10 μL of sample, detection: A254 nm). The results are illustrated in FIGS. 6 and 7B, respectively. The peak observed in the washing samples illustrated in FIG. 6 indicates GSSG, and it was able to be confirmed that $GS(S)_nG$ (n represents 2 or more) was not included in the washed samples, with reference to retention times by HPLC analysis of the GSSG, GSSSG, GSSSSG, and GSSSSSG standard samples illustrated in FIG. 7A-1. In contrast, FIG. 7B illustrates the results of HPLC analysis of the sample just after the synthesis (sample before washing and elution).
11. Among the eluted samples, fractions 2 and 3 were sufficiently mixed and dispensed into 5 mL×4 samples, which were dried and solidified by Centirifugal evaporator CVE-3100 (EYELA) to obtain $GS(S)_nG$ (n represents 2 or more).

Figure 7C:
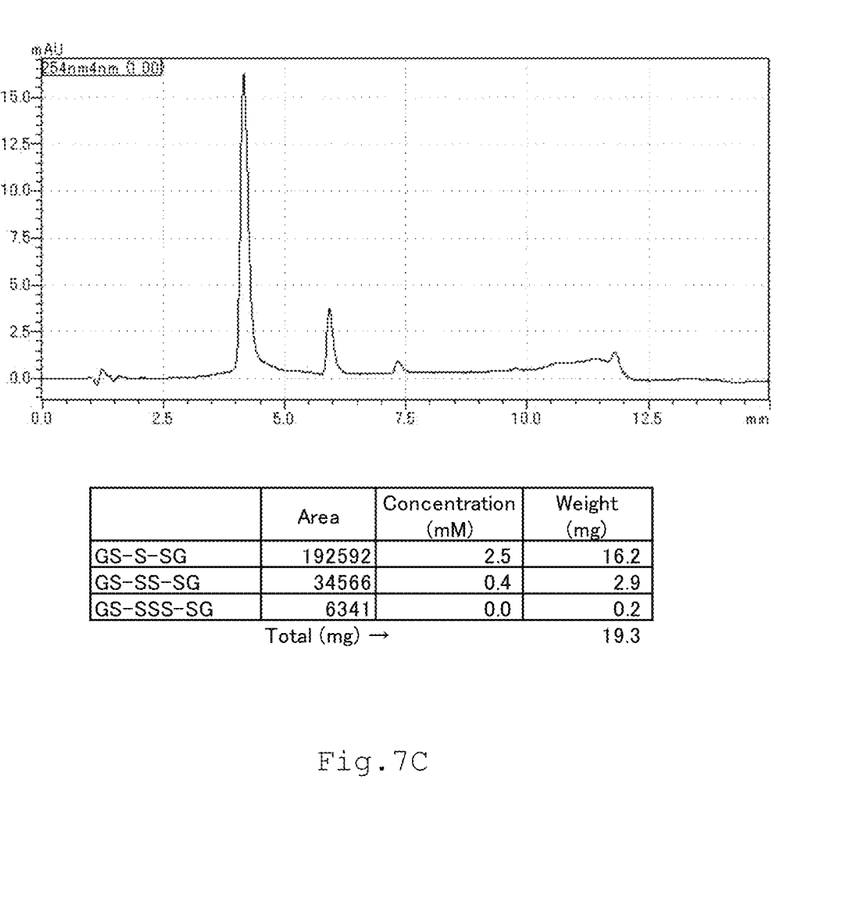
FIG. 7C illustrates a graph (upper) indicating the results of HPLC measurement of an eluted sample and a table (lower) indicating the results of quantification of various active sulfur molecules.

12. In order to quantify obtained GS(S)$_n$G by using HPLC (detection: A254 nm), 1 mM, 100 µM, 50 µM GSSG samples having known concentrations were produced using 10 mM GSSG (5.5 µg of GSSG+897.7 µL of MilliQ water) to generate a standard curve (FIG. 7A-2). As a result of calculation of the content of GS(S)$_n$G in the eluate from the standard curve, the content of the fraction 2 was 19.3 mg. The results are illustrated in FIG. 7C. FIG. 7C illustrates the results of the HPLC analysis of the eluted samples. Since there is no peak at a retention time of 2 min, it was able to be confirmed that GSSG was not included, and GS(S)$_n$G (n represents 2 or more) was eluted. Most of them include GSSSG and GSSSSG, and the amount of GSSSSSG was minute. Since a value at A254 nm at that time was 0.701, the content of the fraction 3 (A254 nm, 0.507) was 13.9 mg, and 33.2 mg in total of GS(S)$_n$G was able to be obtained.

<Investigation of Cytotoxicity in Active Sulfur Molecules>

Figure 8:
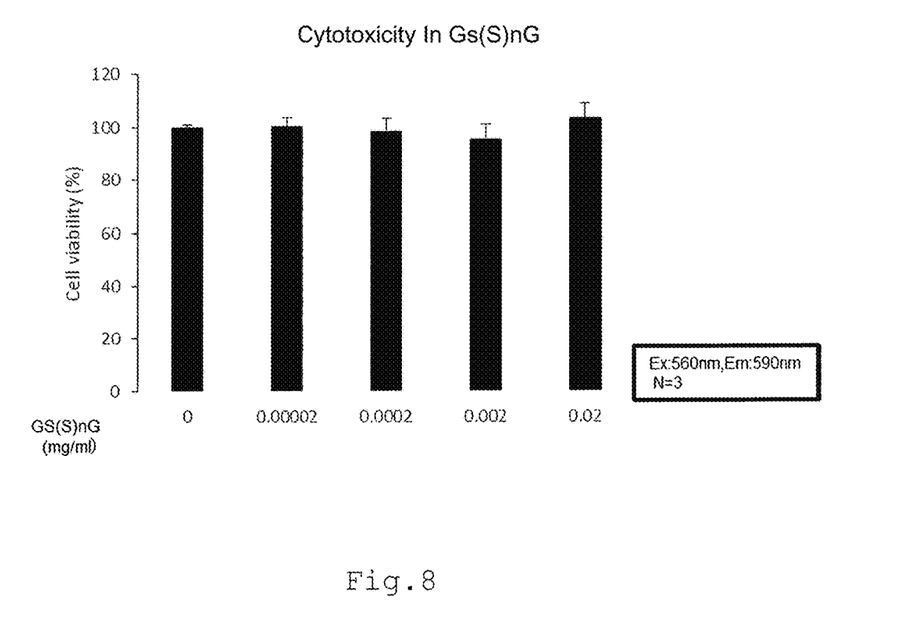
FIG. 8 is a graph indicating the results of a test on cytotoxicity in GS(S)$_n$G.

The cytotoxicity and neuroprotection effect of a cell line derived from retinal ganglion (RGCS cells) using GS(S),G (n represents 2 or more) synthesized as described above were confirmed by in vitro exposure experiment. The RGCS cells were disseminated at 0.75×10$^4$ cells/100 µL on a 96-well plate and cultured overnight. Each GS(S)$_n$G was added to have a final concentration of 0.02 mg/mL, 0.002 mg/mL, 0.0002 mg/mL, or 0.00002 mg/mL and cultured at 37° C. for 24 hours. Then, the viability of the cells was measured by Alamar Blue method. The results are illustrated in FIG. 8. There was no cytotoxicity due to GS(S)$_n$G.

<Investigation 1 of Effect of Protection of Cells by Active Sulfur Molecules>

Figure 9:
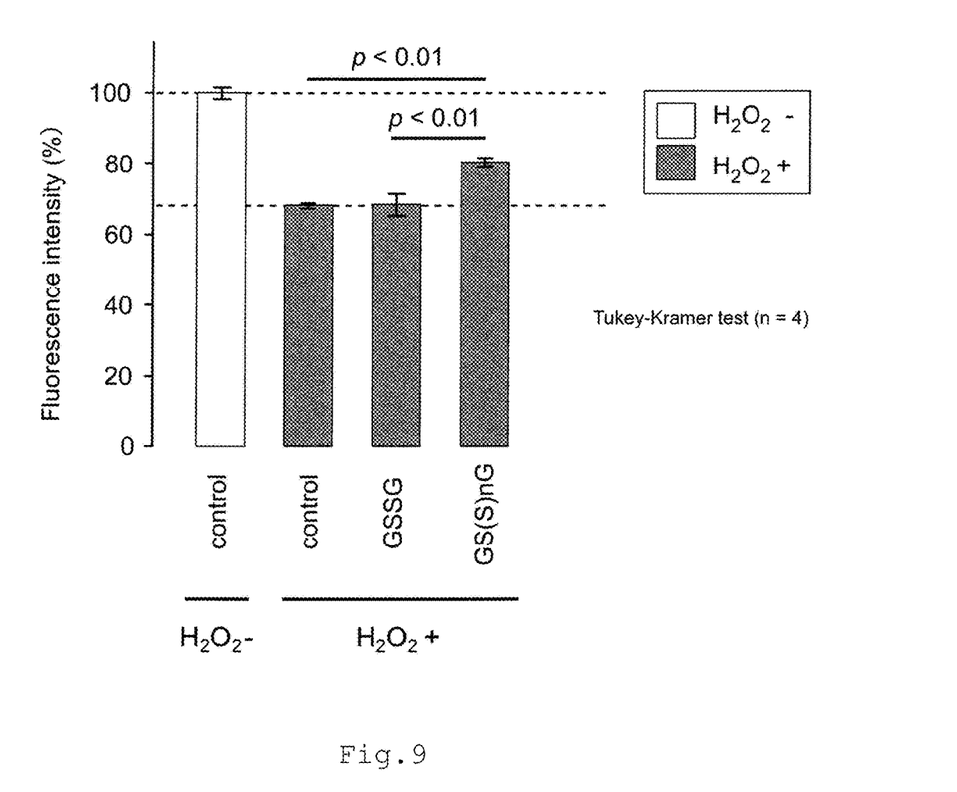
FIG. 9 is a graph indicating the effect of protecting retinal cells in each of GS(S)$_n$G and GSSG.

The effect of protecting the RGCS cells was confirmed by in vitro exposure experiment using GSSG (G4376, SIGMA-ALDRICH) and GS(S)$_n$G (n represents 2 or more) obtained by the above-described method. The RGCS cells were disseminated at 1×10$^4$ cells/100 µL on a 96-well plate and cultured in a medium containing 500 µM BSO (L-buthionine-(S, R)-sulfoximine, Wako Pure Chemical Industries, Ltd.) for 15 hours. Then, each of GS(S)$_n$G and GSSG (final concentration of 25 µg/mL), together with reductase and NADPH, was added to the medium. Instead of the various active sulfur molecules, water in the same amount was added as a control. Hydrogen peroxide (final concentration of 100 µM) was added 6 hours after the addition of the GS(S)$_n$G and and GSSG left to stand for 1.5 hours, and the viability of cells was measured by Alamar Blue method. The results are illustrated in FIG. 9. The results revealed that GS(S)$_n$G exhibits a superior protection effect against cell damage to GSSG.

<Investigation 2 of Effect of Protection of Cells by Active Sulfur Molecules>

Figure 10:
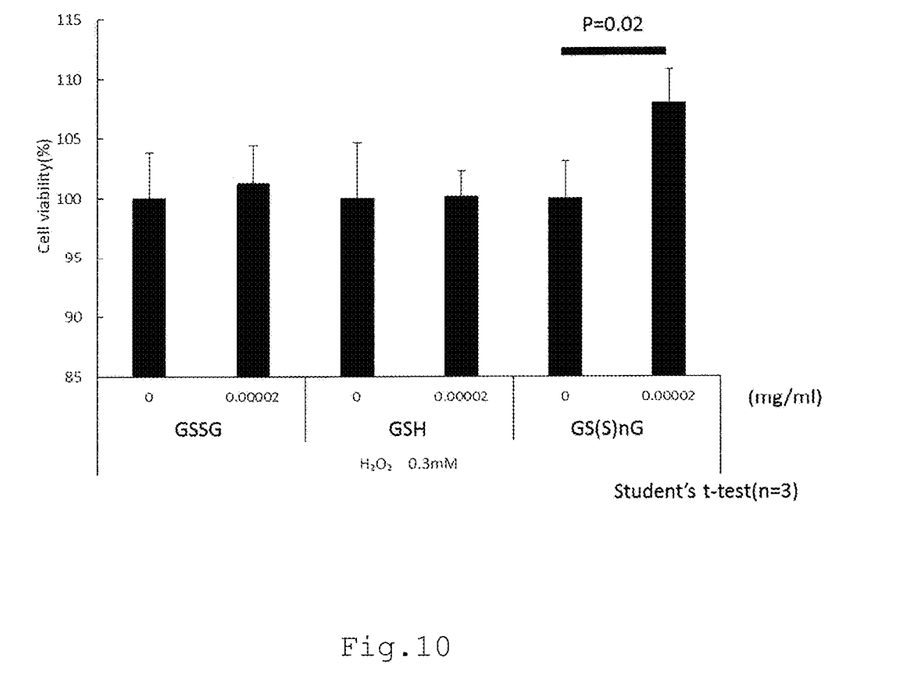
FIG. 10 is a graph indicating the effect of protecting retinal cells at 0.00002 mg/mL in each of GSSG, GSH, and GS(S)$_n$G.

Then, the concentration of active sulfur molecules was changed using GS(S)$_n$G obtained by the above-described method, and the effect of protecting cells was investigated. The RGCS cells were disseminated at 0.75×10$^4$ cells/100 µL on a 96-well plate and cultured overnight. Each of GS(S)$_n$G, GSSG, and GSH (G4251, SIGMA ALDRICH) having a final concentration of 0.00002 mg/mL was added and cultured at 37° C. Hydrogen peroxide (final concentration of 0.3 mM) was added 2 hours after the addition of GS(S)$_n$G, GSSG, and GSH, the culture was further continued for 24 hours, and the viability of cells was measured by Alamar Blue method. The results are illustrated in FIG. 10. The results revealed that GS (S)$_n$G exhibits the effect of protecting cells even at low concentration. This effect was more remarkable than the effects of GSSG and GSH.

<Synergistic Effect with BSS>

Figure 11:
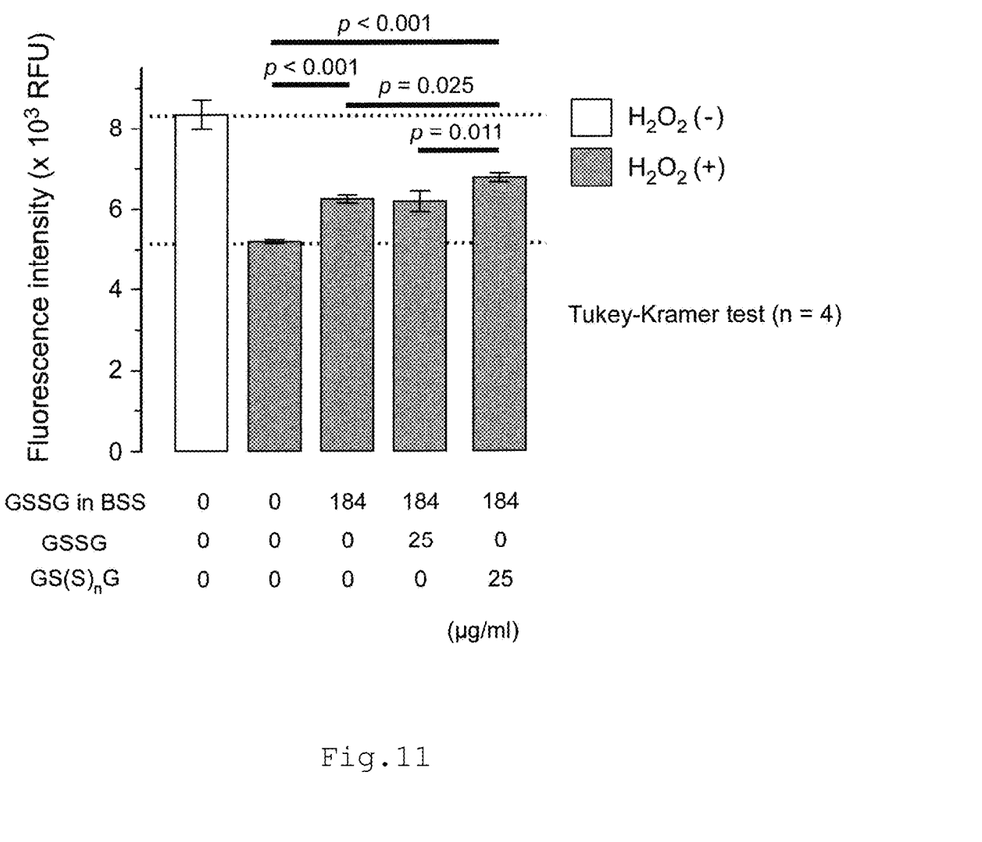
FIG. 11 is a graph indicating the synergistic effects of GSSG and GS(S)$_n$G with BSS in terms of the effect of protecting retinal cells.

The RGCS cells were disseminated at 1×10$^4$ cells/100 µL on a 96-well plate and cultured in a medium containing 500 µM BSO for 15 hours. Then, the medium was removed and replaced with 100 µL of a dilution liquid accompanying 0.0184% BSS PLUS 250 intraocular irrigating solution (including dilution liquid and GSSG stock solution) manufactured by Alcon Japan Ltd. or a dilution liquid (BSS; final concentration of 0.0184%) to which a GSSG stock was added. Subsequently, each of GS(S)$_n$G and GSSG (final concentration of 25 µg/mL), together with reductase and NADPH, was added to the medium. Instead of the solution of the various active sulfur molecules, water in the same amount was added as a control. Hydrogen peroxide (final concentration of 100 µM) and an Alamar Blue detection liquid were added 6 hours after the addition and left to stand for 3 hours, and the viability of cells was measured. The results are illustrated in FIG. 11. In addition to single BSS, GS(S)$_n$G was further added, thereby enhancing the effect of protecting cells.

INDUSTRIAL APPLICABILITY

According to the present invention, there can be provided a novel intraocular irrigating solution with high safety, which has very high antioxidant activity in comparison with a conventional intraocular irrigating solution containing glutathione as an active component and which was able to be confirmed to exist in the eyes not only in patients with intraocular diseases but also in a control group.

The invention claimed is:

1. An intraocular irrigating solution comprising one or more selected from the group consisting of active sulfur molecules represented by Formula (1) and Formula (2), and derivatives of the active sulfur molecules at a concentration of 0.01 µg/mL to 1,000 µg/mL:

$$R_1—S—(S)_n—H \quad (1)$$

wherein R$^1$ is selected from the group consisting of L-cysteine (Cys), homocysteine (Hcys), and glutathione (GSH), and n is an integer 1 or more; and $$R^2—S—(S)_n—R^3 \quad (2)$$

wherein R$^2$ and R$^3$ are independently selected from the group consisting of L-cysteine (Cys), homocysteine (Hcys), and glutathione (GSH), and n is an integer 2 or more.

2. The intraocular irrigating solution according to claim 1, wherein the active sulfur molecules comprise one or more selected from the group consisting of cysteine persulfide and glutathione persulfide.

3. The intraocular irrigating solution according to claim 1, wherein a concentration of the active sulfur molecules in the intraocular irrigating solution is 0.01 µg/mL to 300 µg/mL.

4. The intraocular irrigating solution according to claim 1, wherein a concentration of the active sulfur molecules in the intraocular irrigating solution is 0.01 µg/mL to 100 µg/mL.

5. The intraocular irrigating solution according to claim 1, wherein a concentration of the active sulfur molecules in the intraocular irrigating solution is 0.3 µg/mL to 30 µg/mL.

* * * * *